US012590285B2

(12) United States Patent
Mohandas

(10) Patent No.: US 12,590,285 B2
(45) Date of Patent: Mar. 31, 2026

(54) CULTURE MEDIUM FOR BACTERIA

(71) Applicants: IMU Education SDN BHD, Kuala Lumpur (MY); Kavitha Mohandas, Petaling Jaya (MY)

(72) Inventor: Kavitha Mohandas, Petaling Jaya (MY)

(73) Assignees: IMU EDUCATION SDN BHD, Kuala Lumpur (MY); Kavitha Mohandas, Petaling Jaya (MY)

( * ) Notice: Subject to any disclaimer, the term of this patent is extended or adjusted under 35 U.S.C. 154(b) by 431 days.

(21) Appl. No.: 18/036,870

(22) PCT Filed: Nov. 12, 2021

(86) PCT No.: PCT/MY2021/050100
§ 371 (c)(1),
(2) Date: May 12, 2023

(87) PCT Pub. No.: WO2022/103252
PCT Pub. Date: May 19, 2022

(65) Prior Publication Data
US 2025/0346854 A1 Nov. 13, 2025

(30) Foreign Application Priority Data
Nov. 12, 2020 (MY) ................................ 2020005940

(51) Int. Cl.
*C12N 1/20* (2006.01)
(52) U.S. Cl.
CPC ..................................... *C12N 1/20* (2013.01)

(58) Field of Classification Search
None
See application file for complete search history.

(56) References Cited

U.S. PATENT DOCUMENTS

| | | |
|---|---|---|
| 6,153,422 A | 11/2000 | Ksashiba |
| 2013/0084640 A1 | 4/2013 | Rice et al. |
| 2013/0316343 A1 | 11/2013 | McCarthy et al. |

FOREIGN PATENT DOCUMENTS

| | | |
|---|---|---|
| WO | WO 1993/019161 A1 | 9/1993 |
| WO | WO 2022/103252 A1 | 5/2002 |

OTHER PUBLICATIONS

PCT/MY2021/050100 Internationals Search Report and Written Opinion mailed Feb. 24, 2022.
PCT/MY2021/050100 International Preliminary Report on Patentability mailed May 16, 2023.
Jeong et al., "Composition optimization of cabbage extract medium for cell growth of Lactobacillus plantarum," Korean Society for Biotechnology and Bioengineering Journal, vol. 27, No. 6, pp. 347-351, (2012).

*Primary Examiner* — Oluwatosin A Ogunbiyi
(74) *Attorney, Agent, or Firm* — Alston & Bird LLP

(57) ABSTRACT

An animal-extract free, blood-free and blood-derivative free culture medium formulation is presented. It is developed for growth of fastidious, hemophilic, anaerobic and capnophilic bacteria as well as semi-fastidious and non-fastidious bacteria. The culture medium comprises (i) enriched basal media, (ii) at least one oxygen scavenging agent, (iii) toxic metabolite adsorbent, (iv) growth factor(s) and (v) an active ingredient. The culture medium further includes pH adjuster(s), vitamin, reducing agents and solvent.

11 Claims, No Drawings

CULTURE MEDIUM FOR BACTERIA

FIELD OF THE INVENTION

The present invention relates to culture medium formulation, wherein the culture medium is animal-extract free, blood-free and blood-derivative-free media, in particular, for laboratory isolation and cultivation of fastidious and semi-fastidious, hemophilic bacteria, and also for the cultivation of non-fastidious bacteria.

BACKGROUND OF THE INVENTION

Blood agar or chocolate (heated blood) agar can support growth of non-fastidious and fastidious pathogenic bacteria, wherein the pathogenic bacteria may be aerobic, anaerobic, facultatively anaerobic, microaerophilic and capnophilic respiratory types. Blood agar usually utilizes defibrinated whole blood sourced from animals such as horses, sheep, rams, cows, rabbits or chickens, incorporated into molten basal salts. Meanwhile, chocolate agar utilizes heated, defibrinated whole blood sourced from animals, incorporated into the agar.

Typically, blood agar is a reliable first-line enriched medium for culturing human or animal pathogenic bacteria, in particular, bacteria of unknown identity, for which more specific growth requirements have yet to be elucidated. However, the use of blood-based media has its own shortcomings, wherein it entails the routine collection of blood from slaughter houses or the cultivation and breeding of animals for periodic blood collection. The latter is a labour intensive and expensive activity of dubious ethicality. In some countries, wool sheep, rabbits, cattle, goats and horses are specially bred for this purpose. The cost of breeding animals for generating blood for scientific applications is often prohibitive and also sometimes untenable due to the environment being inhospitable for breeding the animals. As an example, breeding of wool sheep is unfeasible in hot, tropical climates. In such circumstances, human blood is sometimes utilized. However, human blood often fails to accommodate growth of many pathogens, or alternatively, yields colony morphologies or hemolytic patterns that confound pathogen identification. Further, the use of human and animal blood for bacterial cultivation also poses a biosafety risk due to the possible presence of infectious agents such as Bovine Spongiform Encephalitis (BSE)/scrapie prions, *Brucella* spp, Crimean Congo Haemorrhagic Fever Virus (CCHF), anthrax, hepatitis E, human immunodeficiency viruses (HIV) and influenza viruses, amongst others.

Additionally, commercial and laboratory preparation of blood agar is a tedious process. The agar must be maintained at a low temperature to prevent spontaneous thermal lysis of erythrocytes. Minimizing the duration in which whole blood is exposed to hot agar is a challenging task for both commercial and small laboratories.

At times, haemoglobin, haeme or haematin are utilized as a substitute for whole blood in blood-based bacteriological media. These blood-based supplements are often extracted from animal/human blood but is sometimes produced by hemisynthesis or complete laboratory synthesis, the latter of which is an expensive process. In summary, the manufacturing of blood agar is an expensive, labour intensive and tedious endeavor wrought with animal welfare concerns and associated with a high carbon footprint.

In view of the above, an approach has been developed to produce culture media, wherein the culture media is animal-extract free, blood-free and blood-derivative-free, in particular for growth of hemophilic bacteria, wherein the manufacture of the medium is associated with lower cost, lower carbon footprint and lower biosafety risk in comparison to blood-based culture media.

SUMMARY OF THE INVENTION

The present invention discloses animal-extract-free, blood-free and blood-derivative-free culture medium formulation for growth of fastidious and semi-fastidious, hemophilic bacteria and non-fastidious bacteria. The culture medium formulation comprises (i) enriched basal media, (ii) at least one oxygen scavenging agent, (iii) toxic metabolite adsorbent(s), (iv) growth factor(s) and (vii) an active ingredient. The culture medium may further include pH adjuster(s), a vitamin, reducing agent and solvent.

DETAILED DESCRIPTION OF THE INVENTION

A detailed description of the preferred embodiments of the present invention is disclosed herein. It should be understood, however, that the embodiments are merely exemplary of the present invention, which may be embodied in various forms. Therefore, the details disclosed herein are not to be interpreted as limiting, but merely as the basis for the claims and for teaching one skilled in the art of the invention. The numerical data or ranges used in the specification are not to be construed as limiting.

The present invention relates to culture medium formulation wherein the culture medium is completely animal-extract-free, blood-free and blood-derivative-free media, in particular, for growth of fastidious and semi-fastidious, hemophilic bacteria but also for the growth of other non-fastidious bacteria. The present invention describes the use of an active ingredient, in particular, chlorophyll, as a blood replacement for the culture of fastidious, hemophilic bacteria as well as other non-fastidious bacteria.

For the purpose of the present invention, the term "fastidious bacterium" refers to any bacterium that has complex or specific nutritional requirements. The bacterium will only grow if specific nutrients are present in its culture medium.

For the purpose of the present invention, the term "semi-fastidious bacterium" refers to any bacterium that has partially complex or partially specific nutritional requirements. The bacterium will only grow if the partial requirements of specific nutrients are present in its culture medium.

For the purpose of the present invention, the term "non-fastidious bacterium" refers to any bacterium that does not have complex or specific nutritional requirements. The bacterium can grow without the presence of specific nutrients in its culture medium.

For the purpose of the present invention, the term "hemophilic" refers to any bacterium that either has an obligate (strict) requirement for blood for its growth, or alternatively, grows better when supplemented with blood.

The present invention relates to culture medium formulation for growth of fastidious and semi-fastidious, hemophilic bacteria. The culture medium formulation comprises (i) enriched, basal media, (ii) at least one oxygen scavenging agent, (iii) toxic metabolite adsorbent(s), (iv) growth factor(s) and (vii) an active ingredient, all of which are animal-extract-free, blood-free and blood-derivative-free. The culture medium may further include pH adjuster(s), a vitamin, reducing agent and solvent.

3

The enriched basal media are selected from the group comprising soy peptones, agar, vegetable peptones, edestin hydrolysate, legumin hydrolysate, vegetable tryptose and any combinations thereof.

The oxygen scavenging agent is at least one or more selected from the group consisting of L-cysteine, sodium bicarbonate, ferrous pyrophosphate, sodium thioglycolate, sodium sulphide, dithionite, sodium pyruvate, ascorbic acid, butylated hydroxyanisole (BHA), butylated hydroxytoluene (BHT), tocopherols, trolox, catalase, oxyrase enzyme, mixture of glucose oxidase, glucose and catalase and any combinations thereof.

The toxic metabolite adsorbent is selected from the group consisting of soluble starch and activated charcoal and any combinations thereof.

The growth factor is selected from the group consisting of sodium succinate, disodium succinate, sodium chloride, yeast extract, sodium pyrophosphate, sodium pyruvate, arginine, β-NAD, ferric citrate and any combinations thereof.

The active ingredient is selected from the group consisting of plant-based chlorophyll, algal chlorophyll, bacteriochlorophyll, leghemoglobin and any combinations thereof, preferably plant-based chlorophyll. The active ingredient is used in an amount ranging between 2.5-37.5 mg/L. The chlorophyll used in the present invention is a commercially available chlorophyll product but not limited thereto. The person skilled in the art may extract the chlorophyll in the laboratory using known methods.

The pH adjuster is selected from the group consisting of acetic acid, potassium hydroxide and any combinations thereof, used as required to obtain the desired final pH.

The vitamin is selected from the group consisting of Menadione (Vitamin K3) solubilized in Dimethyl Sulfoxide (DMSO), Phylloquinone (Vitamin K1) solubilised in absolute ethanol, 1,4-Dihydroxy-2-Naphthoic Acid (DHNA) solubilised in absolute ethanol and any combinations thereof.

The reducing agent is selected from the group consisting of dithiothreitol, ascorbic acid, cysteine hydrochloride, 2-mercaptoethanol, sodium sulfite or sodium thioglycolate and any combinations thereof.

The solvent is selected from the group consisting of reverse osmosis water and deionized water and any combinations thereof, preferably deionized water. The solvent is used in a required amount to top-up the volume to 100%.

The culture medium formulation of the present invention is used for the cultivation of (i) fastidious, anaerobic, hemophilic bacteria such as *Prevotella melaninogenica, Bacteroides fragilis, Fusobacterium necrophorum* and *Peptostreptococcus anaerobius,* (ii) capnophilic, hemophilic bacteria such as *Haemophilus influenzae,* and (iii) the semi-fastidious, hemophilic bacteria, *Streptococcus pyogenes* and methicillin resistant *Staphylococcus aureus* (MRSA), as well as other, non-fastidious bacteria such as non-drug resistant *Staphylococcus aureus, Escherichia coli* and *Pseudomonas aeruginosa* that do not have obligate or partial requirements for blood for their growth, but are not limited thereto.

The present invention clearly describes the use of plant-based chlorophyll as the active ingredient with a proven role as a growth factor and probable role as a blood replacement for the cultivation of hemophilic bacteria.

The following example is constructed to illustrate the present invention in a nonlimiting sense.

Example 1

A preliminary study was conducted with the fastidious, anaerobic, hemophilic bacterium i.e. *Prevotella melanino-*

4

*genica. Prevotella melaninogenica* was cultivated in culture medium formulation-1 of the present invention. The details of formulation-1 are tabulated in Table 1 below:

TABLE 1

Chemical components and compositions thereof of formulation-1 of the present invention for the fastidious, anaerobic, hemophilic bacterium, *Prevotella melaninogenica.*

| Chemical components | Working range (g/L) | Preferred range (g/L) | Typical value (g/L) |
|---|---|---|---|
| Trypticase Soy Agar | 39.0-41.0 | 39.5-40.5 | 40.0 |
| Sodium Bicarbonate | 0.3-0.5 | 0.35-0.45 | 0.4 |
| Soluble Starch | 0.25-1.75 | 0.5-1.5 | 1.0 |
| Sodium Succinate | 0.4-0.6 | 0.45-0.55 | 0.5 |
| L-Cysteine | 0.3-0.5 | 0.35-0.45 | 0.4 |
| Reverse Osmosis Water | 993-994.5 mL | 993.5-994.5 mL | 994 mL |
| pH adjusted to 7.0 ± 0.1 then autoclaved (121° C., 15 psi, 15 m), cooled and the following additives incorporated: | | | |
| Chlorophyll solution | 4-6 mL | 4.5-5.5 mL | 5 mL |
| Menadione (1 mg/ml in DMSO) | 0.5-1.5 mL | 0.75-1.25 mL | 1.0 mL |

Note:
  i. Trypticase Soy Agar is a commercially available formulation that contains the animal extract, casein i.e. milk protein.
  ii. However, other animal-free extract sources which contain synthetic casein can also be used in the culture media formulation.

A growth assessment study was conducted for *Prevotella melaninogenica.* The relevant supportive laboratory results that have been obtained are tabulated in Table 2 below.

TABLE 2

Comparative growth of *Prevotella melaninogenica* over ten consecutive subcultures on formulation-1 of the present invention, with and without the active ingredient.

| Subculture No. from Frozen Stock | Blood - free medium WITHOUT active ingredient | Blood - free medium WITH active ingredient |
|---|---|---|
| 1st subculture | + + + | + + + |
| 2nd subculture | + + + + | + + + + |
| 3rd subculture | + + + + | + + + + |
| 4th subculture | + | + + + + |
| 5th subculture | 0 | + + + + |
| 6th subculture | 0 | + + + + |
| 7th subculture | 0 | + + + + |
| 8th subculture | 0 | + + + + |
| 9th subculture | 0 | + + + + |
| 10th subculture | 0 | + + + + |

Remarks:
0 = no growth
+ = scanty growth
++ = moderate growth
+ + + = good growth
+ + + + = excellent growth The results show that formulation-1 of the culture medium of the present invention, which is completely blood-free and blood-derivative-free, supports excellent growth of at least one fastidious and hemophilic, anaerobic bacterial pathogen, which is *Prevotella melaninogenica,* commonly cultivated in blood-based media, over ten consecutive subcultures. This indicates that the active ingredient in the medium can consistently support growth of the fastidious and hemophilic, anaerobic bacterium. In the present invention, the active ingredient is plant-based chlorophyll.

Further studies were conducted to negate the use of Trypticase Soy Agar that contains the animal extract, casein. These studies are discussed further in examples 2 to 4 below.

Example 2

The fastidious, anaerobic and hemophilic bacteria, *Prevotella melaninogenica, Bacteroides fragilis, Fusobacterium necrophorum* and *Peptostreptococcus anaerobius* were cultivated on formulation-2 of the present invention. The details of formulation-2 are tabulated in Table 3 below.

TABLE 3

Chemical components and compositions thereof of formulation-2 of the culture medium of the present invention for fastidious, anaerobic, hemophilic bacteria.

| Chemical components | Working range (g/L) | Preferred range (g/L) | Typical value (g/L) |
|---|---|---|---|
| Soy Peptone | 14.0-16.0 | 14.5-15.5 | 15.0 |
| Sodium Chloride | 4.0-6.0 | 4.5-5.5 | 5.0 |
| Vegetable Tryptose | 4.0-6.0 | 4.5-5.5 | 5.0 |
| Sodium Bicarbonate | 0.3-0.5 | 0.35-0.45 | 0.4 |
| Soluble Starch | 0.5-1.5 | 0.75-1.25 | 1.0 |
| Disodium Succinate | 0.4-0.6 | 0.45-0.55 | 0.5 |
| L-Cysteine | 0.45-0.65 | 0.5-0.6 | 0.55 |
| Yeast Extract | 4.0-6.0 | 4.5-5.5 | 5.0 |
| Activated Charcoal | 9.0-11.0 | 9.5-10.5 | 10.0 |
| Agar | 14.0-16.0 | 14.5-15.5 | 15.0 |
| pH adjusted to 7.5 ± 0.1 then autoclaved (110° C., 20 m), cooled and the following additives incorporated: | | | |
| Menadione | 0.0005-0.0015 | 0.00075-0.00125 | 0.001 |
| Dithiothreitol | 0.15-0.35 | 0.2-0.3 | 0.25 |
| Chlorophyll | 0.004-0.006 | 0.0045-0.0055 | 0.005 |
| Sodium Pyruvate | 3.0-5.0 | 3.5-4.5 | 4.0 |
| Sodium Pyrophosphate | 0.15-0.35 | 0.20-0.30 | 0.25 |
| Arginine | 0.5-1.5 | 0.75-1.25 | 1.0 |
| Ferric Citrate | 0.0001-0.0003 | 0.00015-0.00025 | 0.0002 |

A growth assessment study was conducted for the four anaerobic, hemophilic bacterial pathogens (i.e. *Prevotella melaninogenica, Bacteroides fragilis, Fusobacterium necrophorum* and *Peptostreptococcus anaerobius*). The relevant supportive laboratory results that have been obtained are tabulated in Table 4 below.

TABLE 4

Growth index of four fastidious, anaerobic, hemophilic bacterial pathogens when plated at high inoculum density on formulation-2.

| SPECIES | GROWTH INDEX WHEN PLATED AT HIGH INOCULUM DENSITY ON FORMULATION-2 |
|---|---|
| *Prevotella melaninogenica* | + + + + |
| *Bacteroides fragilis* | + + + + |
| *Fusobacterium necrophorum* | + + + + |
| *Peptostreptococcus anaerobius* | + + + + |

Remarks:
0 = no growth
+ = scanty growth
++ = moderate growth
+ + + = good growth
+ + + + = excellent growth The results show that formulation-2 of the present invention, which is both animal-extract-free, blood-free and blood-derivative-free, supports excellent growth of four fastidious, anaerobic, hemophilic bacteria i.e. *Prevotella melaninogenica, Bacteroides fragilis, Fusobacterium necrophorum* and *Peptostreptococcus anaerobius*, all of which are commonly cultivated on blood-based media. In the present invention, the active ingredient is plant-based chlorophyll.

A medium productivity test was conducted to evaluate colony counts of anaerobic bacteria plated at low inoculum density on the test medium (formulation-2) and the reference blood-based medium which was *Brucella* Sheep Blood Agar. The test results for one bacterium, *Bacteroides fragilis*, was further analyzed and is disclosed below in Table 5.

TABLE 5

Medium productivity test results of *Bacteroides fragilis* on formulation-2 of the present invention for anaerobes and the reference blood - based medium.

| | REFERENCE BLOOD BASED MEDIUM | FORMULATION-2 |
|---|---|---|
| Mean Colony Count | 80.4 (n = 5) | 85.0 (n = 3) |
| Standard Deviation | 14.4 | 15.1 |
| Coefficient of Variation | 17.9 | 17.8 |
| Poisson 2-Sample Rate Test (Minitab 20.2) | No significant difference between means at the 95% level of confidence (p = 0.511) | |

The tabulated results above show that the medium productivity level for *Bacteroides fragilis* on formulation-2 of the present invention for anaerobes is comparable to the reference blood-based medium.

Further analyses were conducted to determine the medium productivity for *B. fragilis* on formulation-2 of the present invention, with and without the active ingredient, plant-based chlorophyll.

TABLE 6

Medium productivity test results for *Bacteroides fragilis* on formulation-2 of the present invention for anaerobes, with and without the active ingredient, plant - based chlorophyll

| | FORMULATION-2 (WITH ACTIVE INGREDIENT) | FORMULATION-2 (WITHOUT ACTIVE INGREDIENT) |
|---|---|---|
| Mean Colony Count | 85.0 (n = 3) | 47.3 (n = 3) |
| Standard Deviation | 15.1 | 38.7 |
| Coefficient of Variation | 17.8 | 81.7 |
| Poisson 2-Sample Rate Test (Minitab 20.2) | There is a significant difference between the means at the 95% level of confidence (p = 0.000) | |

Cohen's d=1.283 Indicating a LARGE EFFECT SIZE.

The tabulated results above show that the productivity level of formulation-2 with active ingredient is significantly higher than the productivity level of formulation-2 without active ingredient. Thus, there is a statistically significant effect of the presence of the active ingredient in the culture medium of the present invention and the effect size is large. In the present invention, the active ingredient is plant-based chlorophyll.

Example 3

The capnophilic and hemophilic bacterium, *Haemophilus influenzae*, which has an obligate (strict) requirement for blood (i.e. heme) during aerobic growth, was cultivated on formulation-3 of the culture medium of the present invention. The details of formulation-3 are tabulated in Table 7 below:

TABLE 7

Chemical components and compositions thereof of formulation-3
of the culture medium of the present invention for the capnophilic,
hemophilic bacterium, *H. influenzae*.

| Chemical components | Working range (g/L) | Preferred range (g/L) | Typical value (g/L) |
|---|---|---|---|
| Soy Peptone | 14.0-16.0 | 14.5-15.5 | 15.0 |
| Sodium Chloride | 4.0-6.0 | 4.5-5.5 | 5.0 |
| Vegetable Tryptose | 4.0-6.0 | 4.5-5.5 | 5.0 |
| Agar | 9.0-11.0 | 9.5-10.5 | 10.0 |
| pH adjusted to 7.1 ± 0.2 then autoclaved (110° C., 20 m), cooled and the following additives incorporated: | | | |
| Ferric Citrate | 0.0001-0.0003 | 0.00015-0.00025 | 0.0002 |
| Yeast Extract | 4.0-6.0 | 4.5-5.5 | 5.0 |
| D-Glucose | 1.5-3.5 | 2.0-3.0 | 2.5 |
| L-Cysteine | 0.25-0.45 | 0.30-0.40 | 0.35 |
| Chlorophyll | 0.033-0.037 | 0.034-0.036 | 0.035 |
| B-NAD | 0.010-0.020 | 0.0125-0.0175 | 0.015 |

A growth evaluation study was conducted for *H. influenzae* on formulation-3 of the present invention. The relevant supportive laboratory results that have been obtained are tabulated in Table 8 below.

TABLE 8

Growth index of *H. influenzae* when plated
at high inoculum density on formulation-3.

| SPECIES | GROWTH INDEX WHEN PLATED AT HIGH INOCULUM DENSITY ON FORMULATION-3 |
|---|---|
| *Haemophilus influenzae* | + + + + |

Remarks:
0 = no growth
+ = scanty growth
++ = moderate growth
+ + + = good growth
+ + + + = excellent growth The results above show that the animal-extract-free, blood-free and blood-derivative-free formulation-3 of the culture medium of the present invention supports excellent growth of the capnophilic and hemophilic bacterium, *Haemophilus influenzae*, which is commonly cultivated on blood-based media (Chocolate II Agar with Haemoglobin and NAD). Although, *H. influenzae* has an obligate growth requirement for heme from blood for its aerobic growth, it is still able to grow in animal-extract-free, blood-free and blood-derivative-free formulation-3 of the culture medium of the present invention. This suggests that the active ingredient in formulation-3 is a growth factor for *H. influenzae*, possibly replacing the role of blood heme in supporting aerobic growth of the bacterium. In the present invention, the active ingredient is plant-based chlorophyll.

Table 9 shows the results of medium productivity studies for *H. influenzae* on formulation-3 of the culture medium of the present invention, as compared to the reference blood medium (Chocolate II Agar with Haemoglobin and NAD).

TABLE 9

Medium productivity level for *H.influenzae* on formulation-3
of the culture medium of the present invention as
compared to the reference blood medium

| | REFERENCE BLOOD BASED MEDIUM | FORMULATION-3 |
|---|---|---|
| Mean Colony Count | 21.2 (n = 6) | 17.3 (n = 3) |
| Standard Deviation | 1.3 | 1.5 |
| Coefficient of Variation | 6.3 | 8.8 |
| Poisson 2-Sample Rate Test (Minitab 20.2) | No significant difference between means at the 95% level of confidence (p = 0.255) | |

The tabulated results above show that the medium productivity level for *H. influenzae* on formulation-3 of the present invention for the capnophilic and hemophilic bacterium, is comparable to the reference blood-based medium.

Table 10 below shows the results of the medium productivity test of *H. influenzae* on the culture medium of the present invention i.e. formulation-3 with active ingredient and formulation-3 without active ingredient.

TABLE 10

Results of the medium productivity test of *H.influenzae*
on formulation-3 of the present invention, with active
ingredient and without active ingredient

| | FORMULATION-3 (WITH ACTIVE INGREDIENT) | FORMULATION-3 (WITHOUT ACTIVE INGREDIENT) |
|---|---|---|
| Mean Colony Count | 17.3 (n = 3) | 9.3 (n = 3) |
| Standard Deviation | 1.5 | 0.6 |
| Coefficient of Variation | 8.8 | 6.2 |
| Poisson 2-Sample Rate Test (Minitab 20.2) | There is a significant difference between the means at the 95% level of confidence (p = 0.010) | |

Cohen's d=6.926 Indicating a LARGE EFFECT SIZE.

The tabulated results above show that the productivity level of formulation-3 with active ingredient is significantly higher than the productivity level of formulation-3 without active ingredient. Thus, there is a statistically significant effect of the active ingredient and the effect size is large. In the present invention, the active ingredient is plant-based chlorophyll.

Example 4

The growth of semi-fastidious and non-fastidious bacteria that either have partial (*Streptococcus pyogenes*, Methicillin Resistant *Staphylococcus aureus* i.e. MRSA) or no (*Escherichia coli, Staphylococcus aureus, Pseudomonas aeruginosa*) blood requirements can also be supported by the culture medium of the present invention.

The semi-fastidious, capnophilic and hemophilic bacterium, *S. pyogenes*, was cultivated on formulation-4 of the culture medium of the present invention. The details of formulation-4 are tabulated in Table 11 below:

TABLE 11

Chemical components and compositions thereof of formulation-4 of the culture medium of the present invention for the semi - fastidious, capnophilic, hemophilic bacterium, *S. pyogenes*.

| Chemical components | Working range (g/L) | Preferred range (g/L) | Typical value (g/L) |
|---|---|---|---|
| Soy Peptone | 14.0-16.0 | 14.5-15.5 | 15.0 |
| Sodium Chloride | 4.0-6.0 | 4.5-5.5 | 5.0 |
| Vegetable Tryptose | 4.0-6.0 | 4.5-5.5 | 5.0 |
| Agar | 9.0-11.0 | 9.5-10.5 | 10.0 |
| pH adjusted to 7.5+0.1 then autoclaved (110° C., 20 m), cooled and the following additives incorporated: | | | |
| Yeast Extract | 1.5-3.5 | 2.0-3.0 | 2.5 |
| Sodium Pyruvate | 0.5-1.5 | 0.75-1.25 | 1.0 |
| Chlorophyll | 0.004-0.006 | 0.0045-0.0055 | 0.005 |
| B-NAD | 0.010-0.020 | 0.0125-0.0175 | 0.015 |

Table 12 shows the results of medium productivity studies for *S. pyogenes* on formulation-4 of the culture medium of the present invention, as compared to the reference blood medium (Columbia Sheep Blood Agar).

TABLE 12

Results of medium productivity studies for *S. pyogenes* on formulation-4 of the culture medium of the present invention, as compared to the reference blood medium

| | REFERENCE BLOOD BASED MEDIUM | FORMULATION-4 |
|---|---|---|
| Mean Colony Count | 75.5 (n = 6) | 66.0 (n = 3) |
| Standard Deviation | 2.74 | 1.53 |
| Coefficient of Variation | 3.63 | 2.33 |
| Poisson 2-Sample Rate Test (Minitab 20.2) | No significant difference between means at the 95% level of confidence (p = 0.109) | |

In the data presented above, as there is no significant difference between the means, the medium productivity level for *S. pyogenes* on formulation-4 is comparable to the reference blood based medium.

In addition,

Colony diameter of *S. pyogenes* was larger on formulation-4 (2.0-2.5 mm) than on the reference blood based medium (1.0-1.2 mm).

The productivity of formulation-4 was about 1.88 times higher than on the robust commercially available medium, Trypticase Soy Agar.

Table 13 below shows the results of the medium productivity test of *S. pyogenes* on the culture medium of the present invention i.e. formulation-4 with and without active ingredient.

TABLE 13

Results of the medium productivity test of *S. pyogenes* on formulation-4 with and without active ingredient

| | FORMULATION-4 (WITH ACTIVE INGREDIENT) | FORMULATION-4 (WITHOUT ACTIVE INGREDIENT) |
|---|---|---|
| Mean Colony Count | 66.0 (n = 3) | 42.0(n = 3) |
| Standard Deviation | 1.53 | 2.08 |
| Coefficient of Variation | 2.33% | 4.92% |

TABLE 13-continued

Results of the medium productivity test of *S. pyogenes* on formulation-4 with and without active ingredient

| | FORMULATION-4 (WITH ACTIVE INGREDIENT) | FORMULATION-4 (WITHOUT ACTIVE INGREDIENT) |
|---|---|---|
| Poisson 2-Sample Rate Test (Minitab 20.2) | The difference between the means is statistically significant at the 95% level of confidence (p = 0.000) | |

Cohen's d=13.143 Indicating a LARGE EFFECT SIZE.

The tabulated results above show that the productivity level of formulation-4 with active ingredient is significantly higher than the productivity level of formulation-4 without active ingredient. Thus, there is a statistically significant effect of the active ingredient and the effect size is large. In the present invention, the active ingredient is plant-based chlorophyll.

It is apparent that the animal-extract-free, blood-free and blood-derivative-free culture media of the present invention (formulations 2 to 4) are able to replace conventional blood-based culture media which are used to cultivate hemophilic bacteria.

It is clear that the active ingredient, plant-based chlorophyll, is a growth factor that may be replacing the blood requirement for growth of these bacteria. This could be due to the fact that the heme component of blood hemoglobin and the plant pigment, chlorophyll, are structurally related porphyrins. Both heme and chlorophyll have a protoporphyrin IX (PPIX) skeleton. PPIX is a tetrapyrrole containing 4 methyl, 2 propionic and 2 vinyl side chains. PPIX is a metabolic precursor for hemes, chlorophyll as well as cytochrome c. Heme (i.e. ferro-protoporphyrin IX) is composed of PPIX centrally complexed to iron, whilst chlorophyll is composed of PPIX centrally complexed to magnesium. The structural similarities between heme and chlorophyll may explain their functional convergence and the remarkable ability of blood-free and blood-derivative-free formulations 1 to 4, containing chlorophyll, in enabling excellent growth of hemophilic bacteria.

The manufacture of the culture media of the present invention negates the need for animal husbandry and periodic bleeding of animals. As such, production of the culture media of the present invention is predicted to be considerably cheaper and less labour intensive than production of conventional blood-based culture media. The salient issues of laboratory worker biosafety and safeguarding animal welfare are also adequately addressed by using the present culture media formulations as viable replacements for blood-based and blood-derivative based bacteriological culture media.

Furthermore, as manufacture of the culture media of the present invention is predicted to be cheaper, less labour and energy intensive than the manufacture of blood-based culture media, it would thus generate a lower carbon footprint. As such, it is a more viable, environmentally friendly alternative to the use of blood-based and blood-derivative based bacteriological culture media.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises", "comprising", "including", and "having" are inclusive and therefore specify the presence of stated features, integers, steps, operations, elements, and/or components, but do not preclude the presence or addition of one or more other features, integers, steps, operations, elements, components, and/or groups therefrom.

The method, steps, processes, and operations described herein are not to be construed as necessarily requiring their performance in the particular order discussed or illustrated, unless specifically identified as an order of performance. It is also to be understood that additional or alternative steps may be employed. The use of the expression "at least" or "at least one" suggests the use of one or more elements, as the use may be in one of the embodiments to achieve one or more of the desired objects or results.

The invention claimed is:

1. Culture medium formulation comprising (i) enriched basal media, (ii) at least one oxygen scavenging agent, (iii) toxic metabolite adsorbent(s), (iv) growth factor(s) and (v) active ingredient, wherein the active ingredient is used in an amount ranging between 2.5 to 37.5 mg/L, and wherein the active ingredient is selected from the group consisting of plant-based chlorophyll, algal chlorophyll, bacteriochlorophyll, leghaemoglobin and any combinations thereof.

2. The culture medium as claimed in claim 1, wherein the culture medium formulation further includes pH adjuster(s), vitamin, reducing agent and solvent.

3. The culture medium as claimed in claim 1, wherein the enriched basal media are selected from the group consisting of soy peptones, agar, vegetable peptones, edestin hydrolysate, legumin hydrolysate, vegetable tryptose and any combinations thereof.

4. The culture medium as claimed in claim 1, wherein the oxygen scavenging agent is at least one or more selected from the group consisting of L-cysteine, sodium bicarbonate, ferrous pyrophosphate, sodium thioglycolate, sodium sulphide, dithionite, sodium pyruvate, ascorbic acid, butylated hydroxyanisole (BHA), butylated hydroxytoluene (BHT), tocopherols, trolox, catalase, oxyrase enzyme, mixture of glucose oxidase, glucose and catalase and any combinations thereof.

5. The culture medium as claimed in claim 1, wherein the toxic metabolite adsorbent is selected from the group consisting of soluble starch, activated charcoal and any combinations thereof.

6. The culture medium as claimed in claim 1, wherein the growth factor is selected from the group consisting of sodium succinate, disodium succinate, sodium chloride, yeast extract, sodium pyrophosphate, sodium pyruvate, arginine, β-NAD, ferric citrate and any combinations thereof.

7. The culture medium as claimed in claim 2, wherein the pH adjuster is selected from the group consisting of hydrochloric acid, potassium hydroxide and any combinations thereof.

8. The culture medium as claimed in claim 2, wherein the vitamin is selected from the group consisting of Menadione (Vitamin K3) solubilized in Dimethyl Sulfoxide (DMSO), Phylloquinone (Vitamin K1) solubilised in absolute ethanol, 1,4-Dihydroxy-2-Naphthoic Acid (DHNA) solubilised in absolute ethanol and any combinations thereof.

9. The culture medium as claimed in claim 2, wherein the reducing agent is selected from the group consisting of dithiothreitol, ascorbic acid, cysteine hydrochloride, 2-mercaptoethanol, sodium sulfite or sodium thioglycollate and any combinations thereof.

10. The culture medium as claimed in claim 2, wherein the solvent is selected from the group consisting of reverse osmosis water and deionized water and combinations thereof.

11. The culture medium as claimed in claim 1, wherein the culture medium is animal-extract-free, blood-free and blood-derivative-free.

* * * * *